US008614068B2

(12) United States Patent
Mamalaki et al.

(10) Patent No.: US 8,614,068 B2
(45) Date of Patent: Dec. 24, 2013

(54) PROCESS FOR PRODUCING HEPCIDIN

(75) Inventors: Avgi Mamalaki, Athens (GR); Martha Marinou, Nea Makri Attikis (GR); Vasiliki Koliaraki, Koridallos Attikis (GR)

(73) Assignees: Avgi Mamalake, Athens (GR); Hellenic Pasteur Institute, Athens (GR)

( * ) Notice: Subject to any disclaimer, the term of this patent is extended or adjusted under 35 U.S.C. 154(b) by 484 days.

(21) Appl. No.: 12/675,007

(22) PCT Filed: Aug. 22, 2008

(86) PCT No.: PCT/GR2008/000056
§ 371 (c)(1),
(2), (4) Date: Mar. 2, 2010

(87) PCT Pub. No.: WO2009/027752
PCT Pub. Date: Mar. 5, 2009

(65) Prior Publication Data
US 2011/0097749 A1    Apr. 28, 2011

(30) Foreign Application Priority Data

Aug. 24, 2007 (GR) .................................. 070100553

(51) Int. Cl.
*C12N 15/00* (2006.01)
*C07K 14/435* (2006.01)

(52) U.S. Cl.
USPC ........................ 435/69.1; 435/71.1; 530/324

(58) Field of Classification Search
None
See application file for complete search history.

(56) References Cited

U.S. PATENT DOCUMENTS 7,723,063 B2 *   5/2010  Lauth et al. ................... 435/7.93
2004/0096987 A1   5/2004  Geacintov et al.

FOREIGN PATENT DOCUMENTS

JP    2006-517198         7/2006
WO    2004/058044 A2      7/2004

OTHER PUBLICATIONS

Babitt et al. "Bone Morphogenetic Protein Signaling by Hemojuvelin Regulates Hepcidin Expression", Nature Genetics May 2006, vol. 38, No. 5, p. 531-539.
Bridle et al. "Disrupted Hepcidin Regulation in HFE-associated Haemochromatosis and the Liver as a Regulator of Body Homeostasis", The Lancet Feb. 2003, vol. 361, p. 669-376.
Donovan et al. "The Iron Exporter Ferroportin/Slc40a1 is Essential for Iron Homeostasis", Cell Metabolism Mar. 2005, vol. 1, p. 191-200.
Fleming et al. "Hepcidin: A Putative Iron-Regulatory Hormone Relevant to Hereditary Hemochromatosis and the Anemia of Chronic Disease", PNAS Jul. 2001, vol. 98, No. 15, p. 8160-8162.
Hadley et al. "Iron Absorption by Healthy Women is not Associated with Either Serum or Urinary Prohepcidin", Am. J. Clin. Nutr. 2006, vol. 84, p. 150-155.
Hentze et al. "Balancing Acts: Molecular Control of Mammalian Iron Metabolism", Cell Apr. 2004, vol. 117, p. 285-297.
Hunter et al. "The Solution Structure of Human Hepcidin, A Peptide Hormone With Antimicrobial Activity that is Involved in Iron Uptake and Hereditary Hemochromatosis", The Journal of Biological Chemistry Oct. 2002, vol. 277, No. 40, p. 37597-37603.
Kemna et al. "Time-Course Analusis of Hepcidin, Serum Iron, and Plasma Cytokine Levels in Humans Injected with LPS", Blood 2005, vol. 106, p. 1864-1866.
Kemna et al. "Mass Spectrometry-Based Hepcidin Measurements in Serum and Urine: Analytical Aspects and Clinical Implications" Clinical Chemistry 2007, vol. 53, No. 4, p. 620-628.
Konijn et al. "The Cellular Labile Iron Pool and Intracellular Ferritin in K562 Cells" Blood 1999, vol. 94, p. 2128-2134.
Krause et al. "LEAP-1, A Novel Highly Disulfide-Bonded Human Peptide, Exhibits Antimicrobial Activity", FEBS Letters 2000, vol. 480, p. 147-150.
Murphy et al. "Quantitation of Hepcidin from Human and Mouse Serum Using Liquid Chromatography Tandem Mass Spectrometry", Blood 2007, vol. 110, p. 1048-1054.
Nemeth et al. "Hepcidin, A Putative Mediator of Anemia of Inflammation, is A Type II Acute-Phase Protein", Blood Apr. 2003, vol. 101, No. 7, p. 2461-2463.
Nemeth et al. "Hepcidin Regulates Cellular Iron Efflux by Binding to Ferroportin and Inducing its Internalization", Science 2004, vol. 306, p. 2090-2093.
Nemeth et al. "IL-6 Mediates Hypoferremia of Inflammation by Inducing the Cynthesis of the Iron Regulatory hormone Hepcidin", The Journal of Clinical Investigation May 2004. vol. 113, No. 9, p. 1271-1276.
Nicolas et al. "The Gene Encoding the Iron Regulatory Peptide Hepcidin is Regulated by Anemia, Hypoxia, and Inflammation", The Journal of Clinical Investigation Oct. 2002, vol. 110, No. 7, p. 1037-1044.
Nicolas et al. "Severe Iron Deficiency Anemia in Transgenic Mice Expressing Liver Hepcidin" PNAS Apr. 2002, vol. 99, No. 7, p. 4596-4601.
Park et al. "Hepcidin, A Urinary Antimicrobial Peptide Synthesized in the Liver", The Journal of Biological Chemistry Mar. 2001, vol. 276, No. 11, p. 7806-7810.
Pigeon et al. "A New Mouse Liver-Specific Gene, Encoding a Protein Homologous to Human Antimicrobial Peptide Hepcidin, Is Overexpressed During Iron Overload", The Journal of Biological Chemistry Mar. 2001, vol. 276, No. 11, p. 7811-7819.
Porter et al. "Broad-Spectrum Antimicrobial Activity of Human Intestinal Defensin 5", Infection and Immunity Jun. 1997, vol. 65, No. 6, p. 2396-2401.

(Continued)

*Primary Examiner* — Julie Ha
*Assistant Examiner* — Li Ni Komatsu
(74) *Attorney, Agent, or Firm* — Brooks Kushman P.C.

(57) ABSTRACT

The present invention provides a novel method for producing biologically functional hepcidin in *Pichia pastoris*. The invention further provides novel tagged hepcidin, antibodies and their uses in therapy and immunoassays.

12 Claims, 7 Drawing Sheets

(56) References Cited

OTHER PUBLICATIONS

Figure 1:
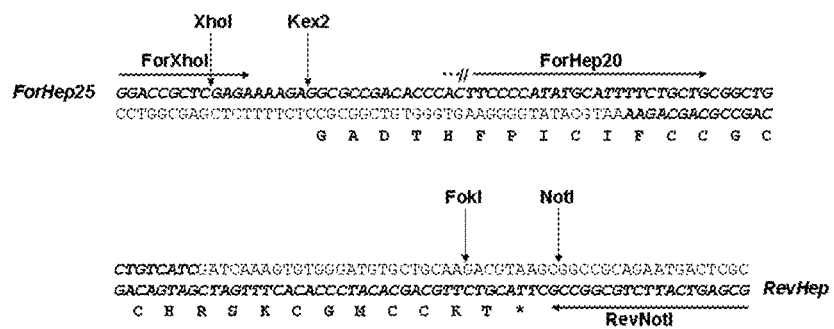

Roetto et al. "Screening Hepcidin for Mutations in Juvenile Hemochromatosis: Identification of a New Mutation", Blood 2004, vol. 103, p. 2407-2409.
Roetto et al. "Mutant Antimicrobial Peptide Hepcidin is Associated wiht Severe Juvenile Hemochromatosis", Nature Genetics Jan. 2003, vol. 33, p. 21-22.
Tomosugi et al. "Detection of Serum Hepcidin in Renal Failure and Inflammation by Using ProteinChip System", Blood 2006, vol. 108, p. 1381-1387.
Wallace et al. "Purification and Partial Characterisation of Recombinant Human Hepcidin", Biochimie 2006, vol. 88, p. 31-37.
Zhang et al. "Expression and Preparation of Recombinant Hepcidin in *Escherichia coli*", Protein Expression and Purification 2005, vol. 41, p. 409-416.
Porto et al. "A Portuguese Patient Homozygous for the −25G>A Mutation of the HAMP Promoter Shows Evidence of Steady-State Transcription but fails to Up-Regulate Hepcidin Levels Iron", Blood 2005, vol. 106, p. 2922-2923.
Gerardi et al. "Recombinant Human Hepcidin Expressed in *Escherichia coli* Isolates as an Iron Containing Protein", Blood Cells, Molecules, and Diseases 2005, vol. 35, p. 177-181.
Hebert et al. "Determination of the Optimal Ammonium Sulfate Concentration for the Fractionation of Rabbit, Sheep, Horse, and Goat Antisera", Applied Microbiology Jan. 1973, vol. 25, No. 1, p. 26-36.
Koliaraki et al. "Iron Regulatory and Bactericidal Properties of Human Recombinant Hepcidin Expressed in *Pichia pastoris*", Biochimie 2008, vol. 90, p. 726-735.
Nemeth et al. "The N-Terminus of Hepcidin is Essential for its Interaction with Ferroportin: Structure-Function Study", Blood Jan. 2006, vol. 107, No. 1, p. 328-333.
Zhang et al. "Cloning and Secretion Expression of Hepcidin in *Pichia pastoris*", Chinese Journal of Biotechnology May 2007, vol. 23, Issue 3, p. 381-385.
Nicolas et al. "Lack of Hepcidin Gene Expression and Severe Tissue Iron Overload in Upstream Stimulatory Factor 2 (USF2) Knockout Mice", PNAS Jul. 17, 2001, vol. 98, No. 15, p. 8780-8785.
Nemeth et al. "Hepcidin is Decreased in TFR2 Hemochromatosis", Blood Feb. 15, 2005, vol. 105, No. 4, p. 1803-1806.
Kemna et al. "Novel Urine Hepcidin Assay by Mass Spectrometry", Blood Nov. 2005, vol. 106, No. 9, p. 3268-3270.
Wallace, Daniel F. et al, "Purification and partial characterisation of recombinant human hepcidin," Biochimie 88, 2006, pp. 31-37.
Zhang, Hui et al., "Cloning and Secretion Expression of Hepcidin in *Pichia pastoris*," Chin J Biotech, 2007 23(3), pp. 381-385.

\* cited by examiner

SEQ ID NO. 1  ICIFCCGCCHRSKCGMCCKT
SEQ ID NO. 2  DTHFPICIFCCGCCHRSKCGMCCKT
SEQ ID NO. 3  GAICIFCCGCCHRSKCGMCCKT
SEQ ID NO. 4  GADTHFPICIFCCGCCHRSKCGMCCKT
SEQ ID NO. 5  GAICIFCCGCCHRSKCGMCCKTFDHHHHHH
SEQ ID NO. 6  GADTHFPICIFCCGCCHRSKCGMCCKTFDHHHHHH
SEQ ID NO. 7  GAICIFCCGCCHRSKCGMCCKLEQKLISEEDLNSAVDHHHHHH
SEQ ID NO. 8  GADTHFPICIFCCGCCHRSKCGMCCKLEQKLISEEDLNSAVDHHHHHH
SEQ ID NO. 9  SMNSRGPAGRLGSVPRAAAAASFLEQKLISEEDLNSAVDHHHHHH

Figure 12.

PROCESS FOR PRODUCING HEPCIDIN

CROSS-REFERENCE TO REALTED APPLICATIONS

This application is the U.S. national phase of PCT Appln. No. PCT/GR08/000056 filed Aug. 22, 2008 which claims priority to Greek Appln. No. 20070100553 filed Aug. 24, 2007, the disclosures of which are incorporated in their entirety by reference herein.

SEQUENCE LISTING

The text file is Sequence_Listing.txt, created Mar. 2, 2010, and of size 4 KB, filed therewith, is hereby incorporated by reference.

The present invention relates to a process for producing a peptide hormone, in particular, hepcidin. In particular, the present invention relates to a process for producing human hepcidin-20 and -25, and analogues thereof, including tagged forms thereof. There is also provided the use of the hepcidin of the present invention as a diagnostic and therapeutic agent.

Iron is an essential trace element for all living organisms due to its involvement in oxygen transport, cell proliferation, respiration and DNA synthesis. However, free iron is extremely toxic and promotes oxidative stress. Mammals do not possess a physiological excretion pathway and iron balance is maintained by the regulation of its absorption and storage (Hentze, M. W., M. U. Muckenthaler, and Andrews N. C. (2004) *Cell* 117, 285-97).

One of the key regulators of human iron metabolism is the peptide hormone, hepcidin (Fleming, R. E. and Sly W. S. (2001) *Proc. Natl. Acad. Sci. U.S.A.* 98, 8160-2). Hepcidin is a small cysteine rich peptide predominantly expressed in the liver (Pigeon, C., Ilyin, G., Courselaud, B., Leroyer, P., Turlin, B., Brissot, P., Loreal, O. (2001) *J. Biol. Chem.* 276, 7811-9) and synthesized as an 84 amino acid pre-propeptide. The mature product, corresponding to the carboxyl terminal region of the pre-propeptide, circulates in two predominant forms of 20 and 25 amino acids and is detectable in human serum and urine (Krause, A., Neitz, S., Magert, H. J., Schulz, A., Forssmann, W. G., Schulz-Knappe, P., Adermann, K. (2000) *FEBS Lett.* 480, 147-50 and Park, C. H., Valore, E. V., Waring, A. J., Ganz, T. (2001) *J. Biol. Chem.* 276, 7806-10). Both isoforms contain eight cysteine residues and give rise to a defensine-like peptide with antibacterial and antifungal activity (Krause, A., Neitz, S., Magert, H. J., Schulz, A., Forssmann, W. G., Schulz-Knappe, P., Adermann, K. (2000) *FEBS Lett.* 480, 147-50 and Park, C. H., Valore, E. V., Waring, A. J., Ganz, T. (2001) *J. Biol. Chem.* 276, 7806-10). NMR-structural studies revealed that hepcidin folds into a simple hairpin that is stabilized by four disulfide bonds, one of them is unusual and forms between two adjacent cysteines in the turn (Hunter, H. N., Fulton, D. B., Ganz, T., Vogel, H. J. (2002) *J. Biol. Chem.* 277, 37597-603).

The involvement of hepcidin in iron metabolism was suggested by experiments showing that its expression is induced by dietary iron (Pigeon, C., Ilyin, G., Courselaud, B., Leroyer, P., Turlin, B., Brissot, P., Loreal, O. (2001) *J. Biol. Chem.* 276, 7811-9). Moreover, mice lacking hepcidin were found to develop a hemochromatosis phenotype with iron deposition in the liver parenchyma and sparing of macrophages (Nicolas, G., Bennoun, M., Devaux, I., Beaumont, C., Grandchamp, B., Kahn, A., Vaulong, S. (2001) *Proc. Natl. Acad. Sci. U.S.A.* 98, 8780-5). On the other hand, transgenic mice over-expressing hepcidin exhibited increased mortality within a few hours after birth due to severe iron deficiency anemia (Nicolas, G., Bennoun, M., Porteu, A., Mativet, S., Beaumont, C., Grandchamp, B., Sirito, M., Sawadogo, M., Kahn, A., Vaulont, S. (2002) *Proc. Natl. Acad. Sci. U.S.A* 99, 4596-601). The molecular mechanism of hepcidin action was elucidated recently when it was found that hepcidin binds to ferroportin, the only known cell iron exporter (Donovan, A., Lima, C. A., Pinkus, J. L., Pinkus, G. S., Zon, L. I., Robine, S., Andrews, N. C. (2005) *Cell Metab.* 1, 191-200), and induces its internalization and degradation in the cytoplasm (Nemeth, E., Tuttle, M. S., Powelson, J., Vaughn, M. B., Donovan, A., Ward, D. M. Ganz, T., Kaplan, J. (2004) *Science* 306, 2090-3). Ferroportin is expressed in hepatocytes, macrophages and enterocytes (Donovan, A., Lima, C. A., Pinkus, J. L., Pinkus, G. S., Zon, L. I., Robine, S., Andrews, N. C. (2005) *Cell Metab.* 1, 191-200). High levels of hepcidin decrease ferroportin expression, thereby inhibiting dietary iron absorption, release of recycled iron from macrophages and mobilization of iron stores from the liver.

Several studies have shown the key role of hepcidin in the control of iron homeostasis. Mutations in hepcidin have been implicated in patients with juvenile hemochromatosis (JH) (Roetto, A., Daraio, F., Porporato, P., Caruso, R., Cox, T. M., Cazzola, M., Gasparini, P, Piperno, A., Camaschella, C. (2004) *Blood* 103, 2407-9 and Roetto, A., Papanikolaou, G., Politou, M., Alberti, F., Girelli, D., Christakis, J., Loukopoulos, D., Camaschella, C. (2003) *Nat. Genet.* 33, 21-2). Moreover, other types of hereditary hemochromatosis, caused by mutations of HFE, TFR2, or HJV genes are also associated with abnormalities in hepcidin expression (Bridle, K. R., Frazer, D. M., Wilkins, S. J., Dixon, J. L., Purdie, D. M., Crawford, D. H., Subramaniam, V. N., Powell, L. W., Anderson, G. J., Ramm, G. A. (2003) *Lancet* 361, 669-73; Nemeth, E., Roetto, A., Garozzo, G., Ganz, T., Camaschella, C. (2005) *Blood* 105, 1803-6 and Babitt, J. L., Huang, F. W., Wrighting, D. M., Xia, Y., Sidis, Y., Samad, T. A., Campagna, J. A., Chung, R. T., Scheyer, A. L., Woolf, C. J., Andrews, N. C., Lin, H. Y. (2006) *Nat. Genet* 38, 531-9).

In chronic inflammatory conditions, hepcidin's upregulation contributes to the anemia of chronic disease (Nemeth, E., Valore, E. V., Territo, M., Schiller, G., Lichtenstein, A, Ganz, T. (2003) *Blood* 101, 2461-3; Nemeth, E., Rivera, S., Gabayan, V., Kellre, C., Taudorf, S., Pedersen, B. K., Ganz, T. (2004) *J. Clin. Invest.* 113, 1271-6 and Nicolas, G., Chauvet, C., Viatte, L., Danan, J. L., Bigard, X., Devaux, I., Beaumont, C., Kahn, A., Vaulont, S. (2002) *J. Clin. Invest* 110, 1037-44).

Because of its profound biomedical significance hepcidin has become the target of intense biochemical studies. However, such studies are hindered by the limited availability of functional peptide. Chemically synthesized hepcidin is commercially available; however, this material is in most cases inactive in biological assays. Isolation of hepcidin from urine has proven to be difficult due to its low concentration. The development of a heterologous system for large-scale production of biologically active hepcidin would be an important step. To date, different approaches have been used to express recombinant hepcidin in *E. coli*. First, hepcidin was expressed as a 10.5 kDa fusion protein (His-hepcidin) in inclusion bodies, purified in denatured form, refolded, cleaved by enterokinase and further purified by reverse-phase chromatography (Zhang, H., Yuan, Q., Zhu, Y., Ma, R., (2005) *Protein Expr. Puff.* 41, 409-16). This peptide exhibited antibacterial activity. In a second approach, hepcidin-20 was cloned as a fusion protein to the C-terminus of GST, or mouse H ferritin, or by inserting it in the middle of the loop between helices D and E of ferritin (Gerardi, G., Biasiotto, G., Santambrogio, P., Zanella, I., Ingrassia, R., Corrado, M. Cavadini, P., Derosas, M., Levi, S., Arosio, P. (2005) *Blood Cells*

*Mol. Dis.* 35, 177-81). These chimerical proteins were isolated in association with iron and did not recapitulate the biological function of hepcidin. Finally, Myc-His tagged human hepcidin was expressed in HEK-293 cells. The recombinant peptide was processed and secreted correctly and was biologically active in antimicrobial assays (Wallace, D. F., Jones, M. D., Pedersen, P., Rivas, L., Sly, L. I., Subramaniam, V. N. (2006) *Biochimie* 88, 31-7). However, no functional assays, of the above recombinant preparations in regulating iron metabolism are described.

Moreover, based on the key role of hepcidin in iron homeostasis and the pathogenesis of iron disorders it is obvious that an easy assay for its measurement in blood or urine would prove extremely useful for the diagnosis of patients with hemochromatosis or anemia of chronic disease. Currently, the concentration of urinary hepcidin is measured using an immuno-dot assay (Nemeth, E., Rivera, S., Gabayan, V., Kellre, C., Taudorf, S., Pedersen, B. K., Ganz, T. (2004) *J. Clin. Invest.* 113, 1271-6), SDS-PAGE and Western Blot (Nemeth, E., Valore, E. V., Territo, M., Schiller, G., Lichtenstein, A, Ganz, T. (2003) *Blood* 101, 2461-3), or a SELDI-TOF-MS (Kemna, E., Tjalsma, H., Laarakkers, C., Nemeth, E., Williams, H., and Swinkels, D. (2005) *Blood* 106, 3268-3270). Recently, two reports described the use of SELDI-TOF-MS to determine hepcidin concentration in human plasma and serum (Tomosugi, N., Kawabata, H., Wakatabe, R., Higuchi, M., Yamaya, H., Umehera, H., Ishikawa, I. (2006) *Blood* 108, 1381-7 and Kemna, E., Tjalsma, H., Podust, V., and Swinkels, D. (2007) *Clin Chem.* 53, 1-9), whereas according to another report, active human and mouse hepcidin in serum was determined using LC/MS/MS, at the quantitative range of 1 to 500 ng/mL serum for normal human hepcidin (Murphy, A. T., Witcher, D. R., Luan, P., and Wroblewski, V. J. (2007) *Blood* 110, 1048-54).

Despite the utility of these methods for research purposes, the advanced technology of mass spectrometry is not widely accessible for clinical use. The only immunoassay method described so far measures pro-hepcidin, the 84 amino acid precursor of the active hepcidin peptide, and is based on the assumption that serum hepcidin concentrations would be directly correlated to measured pro-hepcidin concentrations (Hadley, K. B., Johnson, L. K., and Hunt, J. R. (2006) *Am. J. Clin. Nutr.* 84, 150-155). However, according to another study using the pro-hepcidin ELISA, serum pro-hepcidin levels do not correlate with urinary hepcidin levels after LPS injection, rendering doubtful the utility of pro-hepcidin measurement for diagnosis (Kemna, E., Pickkers, P., Nemeth, E., van der Hoeven, H., and Swinkels, D. (2005) *Blood* 106, 1864-1866).

In the light of the above, it is evident that there is a need to provide a process which can produce functional recombinant hepcidin in sufficient quantities for advanced research or clinical use and/or the need to provide an assay that can reliably measure the amount of hepcidin in a biological sample, that is, for diagnostic purposes.

It is the aim of the present invention to provide such a process and/or an assay.

In a first aspect of the present invention there is provided a method for producing biologically functional hepcidin or a biologically functional hepcidin derivative, the method including the step of exogenously expressing hepcidin or a derivative within an expression system characterized in that the expression system is a eukaryotic methylotropic yeast, preferably *Pichia pastoris* (*P. pastoris*).

In a second aspect of the present invention there is provided a method for producing biologically functional hepcidin or a biologically functional hepcidin derivative, the method including the step of expressing hepcidin or derivative within an expression system, wherein the hepcidin or derivative is provided with at least one tag at the C-terminal region.

As will be seen by way of reference to the experimental protocols and attached figures below, the present inventors have provided the first successful heterologous expression of a recombinant biologically functional hepcidin or biologically functional derivative of hepcidin. By biologically functional, it is to be understood that the hepcidin and hepcidin derivative are both bactericidal and have the ability to control cellular iron metabolism. It will be appreciated that by comparison with previous attempts to produce recombinant hepcidin, the present method or process has the advantage of soluble expression and high yield without the need of any renaturation process (Zhang, H., Yuan, Q., Zhu, Y., Ma, R., (2005) Protein Expr. Purif. 41, 409-16 and Wallace, D. F., Jones, M. D., Pedersen, P., Rivas, L., Sly, L. I., Subramaniam, V. N. (2006) *Biochimie* 88, 31-7). More importantly, the resulting hepcidins and derivatives are functional not only as antimicrobial peptides but also, or mainly, as a regulator of cellular iron metabolism i.e. they are biologically functional.

It is to be understood that the word "hepcidin" or abbreviation "Hep" as used herein, and unless otherwise specified, covers both human hepcidin-20 and hepcidin-25, namely, the two predominant mature forms of the human hormone hepcidin, which are 20 and 25 amino acid residues long, respectively and hepcidin derivatives. In this respect, human hepcidin-20 is designated herein as Hep20 and has the amino acid sequence of SEQ ID NO. 1 and human hepcindin-25 is designated herein as Hep25 and has the amino acid sequence of SEQ ID NO.2. The word "derivative" as used herein, and unless otherwise specified, includes both the 20 and 25 amino acid residues of human hepcidin-20 and hepcidin-25 with one or more additional amino acids positioned at the N terminus. It is also to be understood that unless otherwise specified, the word "hepcidin" or abbreviation "Hep" or "derivative" is not limited to human hepcidin, including human Hep-20 and Hep-25.

Preferably, the derivative is hepcidin-20 or hepcidin-25 with two additional amino acids positioned at the N terminus. In a preferred embodiment, the derivative is hepcidin-20 with additional amino acids glycine and alanine at the N terminal; this derivative is designated herein as hepcidin-20d and has the amino acid sequence of SEQ ID NO. 3. In a further preferred embodiment, the derivative is hepcidin-25 with additional amino acids glycine and alanine at the N terminal; this derivative is designated herein as hepcidin-25d and has the amino acid sequence of SEQ ID NO. 4.

Preferably, the tag is a polyhistidine tag. As will be appreciated, a polyhistidine tag is an amino acid motif that consists of at least six histidines (His). A polyhistidine tag is also known as a hexa-histidine tag, a 6xHis-tag and by the trade marked name, His-tag®. It is to be understood that unless otherwise stated, the abbreviation "His" used throughout means a polyhistidine tag.

Further preferably, the tag is a myc-His-tag. As stated above, the designation "His", unless otherwise stated, means a polyhistidine tag. The designation of "myc" is a c-myc epitope.

It is to be understood that the tag is provided directly or indirectly with the C terminal of the hepcidin or a hepcidin derivative. When provided directly, the tag is positioned consecutive to the terminal amino acid of hepcidin-20 and hepcidin-25 or a hepcidin derivative. The tag may be provided indirectly via a linker.

Preferably, the linker is one or more amino acids positioned consecutive to the terminal amino acid of hepcidin-20 and hepcidin-25 or a hepcidin derivative. More preferably the linker is two amino acids long and, even more preferably; the amino acids are phenylalanine and aspartic acid.

Alternatively, the linker is one or more amino acid substitutions of the terminal amino acids of hepcidin-20, hepcidin-25 or a hepcidin derivative. More preferably, the linker is a single amino acid substitution of the terminal amino acid of hepcidin-20, hepcidin-25 or a hepcidin derivative and, even more preferably, the terminal amino acid threonine is substituted with leucine.

Advantageously, the His tag is provided to the hepcidin-20 or hepcidin-25 with a linker of phenylalanine and aspartic acid. More advantageously, the myc-His tag is provided to the hepcidin-20 or hepcidin-25 with a linker of leucine that has substituted the terminal amino acid threonine.

In a preferred embodiment, the His tag is provided to a derivative of hepcidin-20 having glycine and alanine positioned at the N terminal with a linker of phenylalanine and aspartic acid; this tagged biologically functional hepcidin derivative is designated herein as hepcidin-20His (Hep-20His) and has the amino acid sequence of SEQ ID NO. 5.

In a further preferred embodiment, the His tag is provided to a derivative of hepcidin-25 having glycine and alanine positioned at the N terminal with a linker of phenylalanine and aspartic acid; this tagged biologically functional hepcidin derivative is designated herein as hepcidin-25His (Hep-25His) and has the amino acid sequence of SEQ ID NO. 6.

In a further preferred embodiment, the myc-His tag is provided to a derivative of hepcidin-20 having glycine and alanine positioned at the N terminal with a linker of leucine that substitutes the terminal amino acid threonine; this tagged biologically functional hepcidin derivative is designated herein as hepcidin-20MycHis (Hep-20MycHis) and has the amino acid sequence of SEQ ID NO. 7.

In a further preferred embodiment, the myc-His tag is provided to a derivative of hepcidin-25 having glycine and alanine positioned at the N terminal with a linker of leucine that substitutes the terminal amino acid threonine; this tagged biologically functional hepcidin derivative is designated herein as hepcidin-25MycHis (Hep-25MycHis) and has the amino acid sequence of SEQ ID NO. 8.

Advantageously, the tagged biologically functional hepcidin or a tagged biologically functional hepcidin derivative is exogenously expressed within an expression system, wherein the expression system is a eukaryotic methylotropic yeast, preferably *Pichia pastoris* (*P. pastoris*). With reference to the results given below, it will be appreciated that the expression system of the eukaryotic methylotrophic yeast *P. pastoris* is particularly advantageous due to its ability to produce extracellular soluble proteins, eukaryotic post-translational modifications (such as disulfide bond forming). It is also easy to handle, and has a high yield of production.

Preferably, and prior to expression of hepcidin or a hepcidin derivative, the methods of the present invention include the step of introducing a vector including a hepcidin encoding polynucleotide insert into the expression system, preferably a eukaryotic methylotropic yeast expression system, preferably *Pichia pastoris* (*P. pastoris*).

As used herein, it is to be understood that a hepcidin encoding polynucleotide insert is a polynucleotide which can encode a hepcidin, including human hepcidin-20 and -25 (human Hep20 and Hep25) having the sequence of SEQ ID NOs. 1 and 2 respectively, or a hepcidin derivative, including hepcidin-20d and hepcidin-25d having the sequences of SEQ ID NOs. 3 and 4 respectively. The hepcidin encoding polynucleotide insert also includes a polynucleotide which can encode tagged hepcidin or a tagged hepcidin derivative, including the preferred tags, namely, Myc and 6xHis; and/or the linkers, namely, phenylalanine and aspartic acid or a single leucine amino acid substitution of the terminal amino acid of hepcidin-20 and -25; including hepcidin-20His having the sequence of SEQ ID NO. 5, hepcidin-25His having the sequence of SEQ ID NO. 6, hepcidin-20MycHis having the sequence of SEQ ID NO. 7 and hepcidin-25MycHis having the sequence of SEQ ID NO. 8.

A skilled person will appreciate that the vector may be any suitable vector. For example, the vector may be pPICZαA, pPICZαB or pPICZαC (Invitrogen, Carlsbad, Calif.). The vector can encode the preferred tags, namely, Myc and 6xHis; and/or the linkers, namely, phenylalanine and aspartic acid or a single leucine amino acid substitution of the terminal amino acid of hepcidin-20 and -25.

Advantageously, the hepcidin encoding polynucleotide insert is provided with a FokI restriction site. The unique FokI restriction site of the insert in combination with the restriction sites from the vector enables the construction of Hep-25MycHis, Hep-20MycHis, Hep-25His and Hep-20His plasmids, which permitted the expression of hepcidin-25 and hepcidin-20 and hepcidin derivatives fused to c-MycHis or His epitope alone.

Preferably, a hepcidin encoding polynucleotide insert encodes human hepcidin-25d and the method further includes the step of obtaining the hepcidin-25d encoding insert by PCR amplification of the product obtained by the extension of the overlapping oligonucleotides designated herein as ForHep25 and RevHep; the sequences of which are shown in FIG. 1. Further preferably, PCR amplification is carried out using the primers designated herein as ForXhoI and RevNotI; the sequences of which are shown in FIG. 1.

Advantageously, the hepcidin encoding polynucleotide insert encodes human hepcidin-20d, and the method includes the step of carrying out PCR amplification on the resulting vector, preferably using the primers designated herein as Forhep20 (5-GCGAGTGCATCGACGGCGCCATATG-CATCTTCTGCTG-3) and the RevNotl, the sequence of which is shown in FIG. 1.

Preferably, the methods of the present invention further include the step of purifying the expressed hepcidin. In a preferred embodiment, the step of purifying 5 comprises a two stage purification process. Advantageously the first stage of the purification process comprises metal affinity chromatography. Preferably, the metal is nickel, colbalt or nickel coordinated with nitilotriacetic acid (NTA). In a preferred embodiment the second stage of the purification process comprises gel filtration chromatography. Advantageously, a sepharose or Superdex™ peptide column is used.

Further preferably, the expressed hepcidin is human hepcidin, preferably selected from the group consisting of hepcidin-20 having the sequence of SEQ ID NO. 1, hepcidin-25 having the sequence of SEQ ID NO. 2, hepcidin-20d having the sequence of SEQ ID NO. 3, hepcidin-25d having the sequence of SEQ ID NO. 4, hepcidin-20His having the sequence of SEQ ID NO. 5, hepcidin-25His having the sequence of SEQ ID NO. 6, hepcidin-20MycHis having the sequence of SEQ ID NO. 7 and hepcidin-25MycHis having the sequence of SEQ ID NO. 8.

In a further aspect of the present invention there is provided a hepcidin obtainable by carrying out the method(s) of the present invention.

Advantageously, the hepcidin is human hepcidin-25His having the sequence of SEQ ID NO. 6. With reference to the protocols below, human hepcidin-25His (Hep-25His) was unequivocally the most functional. It exhibited the maximum bactericidal activity against *E. coli* strain ML35, very similar to natural hepcidin25, isolated from urine or synthetic hepcidin. According to Park, C. H., Valore, E. V., Waring, A. J., Ganz, T. (2001) *J. Biol. Chem.* 276, 7806-10, 1000-fold reduction of surviving bacteria ML35p was achieved at 30 µM concentration of both hep25 and hep20. Hep-25His also reduced 1000-fold the number of surviving bacteria at 30 µM. Furthermore, the Hep-25His peptide was also able to elicit a decrease in ferroportin levels by ~50% in target RAW 264.7 macrophages. This effect was apparently due to the internalization and degradation of the transporter ferropotin (FPN1). This mechanism of action was tested in the HEK293-Fpn stable cell line and showed that treatment with the recombinant peptide Hep25-His causes the internalization of FPN1-GFP, by analogy to the synthetic hepcidin, Hep25 (Nemeth, E., Tuttle, M. S., Powelson, J., Vaughn, M. B., Donovan, A., Ward, D. M. Ganz, T., Kaplan, J. (2004) *Science* 306, 2090-3). The concomitant Hep-25His-mediated decrease in TfR1 expression by ~50% is consistent with a homeostatic response to intracellular iron accumulation, which is predicted in cells expressing fewer iron exporting molecules. The retention of iron within Hep-25His-treated RAW 264.7 macrophages is demonstrated by the increase in LIP levels. The data with the negative peptide of 4.8 kDa, produced in *P. pastoris* by the vector alone and bearing a Myc-His tag, indicate the specificity of this response. Moreover we demonstrate that the recombinant peptide can specifically bind to its receptor (ferroportin) by a cross-linking and pull-down assay.

According to the results given below it is clear that Hep-25His, having the sequence of SEQ ID NO. 6, is a very good analogue of hepcidin-25, mimicking its behaviour. It is expressed in high quantity that can be further increased with scaling up to fermentation. In comparison with previous attempts to produce recombinant hepcidin, our system offers the advantage of soluble expression at high yield and without the need of any renaturation procedure (Zhang, H., Yuan, Q., Zhu, Y., Ma, R., (2005) Protein Expr. Purif. 41, 409-16 and Wallace, D. F., Jones, M. D., Pedersen, P., Rivas, L., Sly, L. I., Subramaniam, V. N. (2006) *Biochimie* 88, 31-7). More importantly we report that the recombinant Hep-25His, having the sequence of SEQ ID NO. 6, expressed in yeast *P. pastoris* is functional not only as an antimicrobial peptide but also as a regulator of cellular iron metabolism.

In another aspect of the present invention there is provided the use of any one of the primers selected from the group consisting of ForHep20, ForHep25, RevHep, ForXhoI and RevNotI; the sequences of which are shown in FIG. 1, to amplify a hepcidin encoding polynucleotide, preferably a human hepcidin-20 having the sequence of SEQ ID NO. 1, hepcidin-25 having the sequence of SEQ ID NO. 2, hepcidin-20d having the sequence of SEQ ID NO. 3 or hepcidin-25d having the sequence of SEQ ID NO. 4, encoding polynucleotide.

There is also provided the use of a eukaryotic methylotropic yeast expression system, preferably *Pichia pastoris* (*P. pastoris*), to express hepcidin, preferably human hepcidin including hepcidin-20 having the sequence of SEQ ID NO. 1, hepcidin-25 having the sequence of SEQ ID NO. 2, hepcidin-20d having the sequence of SEQ ID NO. 3, hepcidin-25d having the sequence of SEQ ID NO. 4, hepcidin-20His having the sequence of SEQ ID NO. 5, hepcidin-25His having the sequence of SEQ ID NO. 6, hepcidin-20MycHis having the sequence of SEQ ID NO. 7 and hepcidin-25MycHis having the sequence of SEQ ID NO. 8.

In another aspect of the present invention there is provided, a tagged hepcidin, preferably human hepcidin selected from the group consisting of hepcidin-20His having the sequence of SEQ ID NO. 5, hepcidin-25His having the sequence of SEQ ID NO. 6, hepcidin-20MycHis having the sequence of SEQ ID NO. 7 and hepcidin-25MycHis having the sequence of SEQ ID NO. 8. Advantageously, the hepcidin is human hepcidin-25His having the sequence of SEQ ID NO. 6.

In a further aspect of the present invention, there is provided an antibody that specifically binds to a tagged hepcidin or tagged hepcidin derivative of the present invention. "Specifically binds" refers to a special and precise interaction between two molecules which is dependent on their structure.

There is also provided the use of the tagged hepcidin or tagged hepcidin derivative of the present invention to raise antibodies, preferably monoclonal or polyclonal antibodies. Advantageously, the antibody is a polyclonal antibody obtained by immunizing a rabbit with human Hepcidin-25His. Antibodies or fragments thereof suitable for use in accordance with the present invention include chimeric antibodies, humanized antibodies, single chain antibodies, Fab fragments, Fc fragments, antibody-peptide fusion proteins and monomers or dimmers of the light and heavy chains or mixtures thereof.

In a further aspect of the present invention there is provided the hepcidin or a hepcidin derivative of the present invention for use in therapy, including for use as an antibacterial agent.

In a further aspect of the invention there is provided the hepcidin or hepcidin derivative of the present invention for use in controlling iron metabolism. The hepcidin or hepcidin derivative prevents iron uptake. There is also provided the use of an inhibitor of the hepcidin or hepcidin derivative of the present invention for use in controlling iron metabolism. The inhibitor increases iron uptake.

There is also provided the use of an antibody of the present invention to detect hepcidin or hepcidin derivative levels within a sample. In a preferred embodiment, the sample is a serum sample, preferably human serum, or urine. Advantageously, the hepcidin being detected is human hepcidin-20d or -25d within a sample.

In another aspect of the present invention, there is provided the use of the antibody of the present invention in a competition ELISA assay to determine the amount of hepcidin or a hepcidin derivative within a sample, preferably a human serum sample. Advantageously, the antibody is used to determine the amount of human hepcidin-20d or -25d within a sample.

In a further aspect of the invention there is provided a method for determining the amount of hepcidin within a serum sample, the method comprising the steps of
a) Contacting a serum sample with an antibody and immobilised hepcidin, wherein the antibody specifically binds to the immobilised hepcidin and the hepcidin within the serum sample;
b) Measuring the amount of antibody bound to the immobilised hepcidin; and
c) Comparing the measured amount to a standard thereby determining the amount of hepcidin within the serum sample.

The assay of the present invention, namely, an ELISA method of hepcidin measurement provides several advantages including negating the need for sample pre-treatment, it is simple, quick, highly reproducible and specific and can be widely applied in all clinical and research laboratories. It enables hepcidin to be routinely measured in clinical diagnostic tests as a protein indicator of iron related diseases and contributes to the quick diagnosis and monitoring of their progress.

In an advantageous embodiment, the standard is an inhibition curve generated by the steps of:
a) Contacting a sample containing a known concentration of hepcidin with an antibody and immobilised hepcidin, wherein the antibody specifically binds to both hepcidin and the immobilised hepcidin;
b) Measuring the amount of antibody bound to the immobilised hepcidin;
c) Recording the result, and
d) Repeating the cycle of steps a) to c) using a further sample containing a known concentration of hepcidin which differs from the concentration used in step a) of the previous cycle; and
e) Repeating step d) until such time as a suitable standard curve has been generated.

It is to be understood that the immobilised hepcidin may be hepcidin-20 having the sequence of SEQ ID NO. 1, hepcidin-25 having the sequence of SEQ ID NO. 2, hepcidin-20d having the sequence of SEQ ID NO. 3, hepcidin-25d having the sequence of SEQ ID NO. 4, hepcidin-20His having the sequence of SEQ ID NO. 5, hepcidin-25His having the sequence of SEQ ID NO. 6, hepcidin-20MycHis having the sequence of SEQ ID NO. 7 and hepcidin-25MycHis having the sequence of SEQ ID NO. 8. Preferably, the immobilised hepcidin is hepcidin-25His having the sequence of SEQ ID NO. 6.

Advantageously, the standard is obtained using samples containing known amounts of hepcidin-25His having the sequence of SEQ ID NO. 6.

In a further aspect of the invention there is provided an ELISA kit for use in determining the amount of hepcidin within a serum sample comprising hepcidin; and an antibody which specifically binds to the hepcidin and the hepcidin to be determined. Advantageously, the hepcidin is immobilised. Preferably, the kit further comprises a plurality of containers or vessels, each of which comprising hepcidin at different concentrations to one another.

There is also provided the use of tagged hepcidin of the present invention for treating or preventing hemochromatosis, or a disease resulting therefrom or any other condition associated with iron overload. The disease resulting therefrom may be selected from the group consisting of hepatocarcinoma, cardiomyopathy or diabetes. The tagged hepcidin and tagged hepcidin derivative regulate iron metabolism by preventing iron uptake.

There is also provided the use of an inhibitor of the tagged hepcidin of the present invention for treating or preventing anaemia or a disease resulting therefrom or a condition associated with low levels of iron. In an advantageous embodiment the inhibitor is an antibody of the invention. The inhibitor regulates iron metabolism by increasing iron uptake or neutralizing high levels of hepcidin.

It is to be understood that the tagged hepcidin of the present invention includes hepcidin-20His having the sequence of SEQ ID NO. 5, hepcidin-25His having the sequence of SEQ ID NO. 6, hepcidin-20MycHis having the sequence of SEQ ID NO. 7 and hepcidin-25MycHis having the sequence of SEQ ID NO. 8.

The present invention will now be exemplified by way of reference to the following figures, together with the non-limiting experimental protocols described below carried out by the present inventors in which:

FIG. 1. Cloning procedure of Hep25 and Hep20 in the vector pPICZαC of *P. pastoris*.

The long overlapping oligonucleotides (For Hep25 and RevHep) used for extension are shown in bold Italics. The short primers (For Xho, RevNotI) for PCR of Hep25 and the For Hep20 used for PCR of Hep20 are noted by long arrows. XhoI and NotI restriction sites used to clone the hepcidin PCR products into pPICZαC vector are noted, as well as the FokI site used for constructed tagged peptides. Kex2 cleavage site was placed ahead of hepcidin's DNA sequence, since in previous studies an inefficiency of STE13 protease was observed resulting in a secreted protein containing an additional tetrapeptide.

Figure 2:
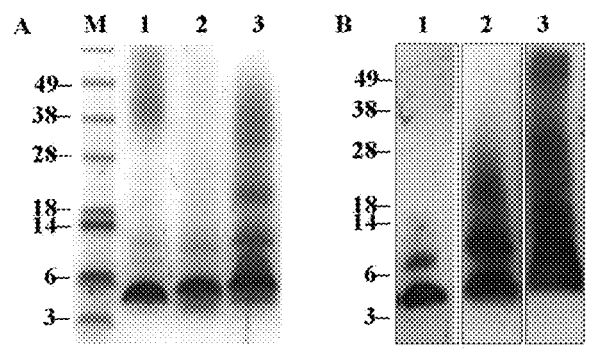

FIG. 2. Analysis of purified tagged hepcidin after Ni-NTA chromatography. Electrophoresis of tagged hepcidins after Ni-NTA purification on a Nu-PAGE 4-12% gel under non-denaturing conditions, followed by Coomasie blue staining A, and Western blot using anti-His mAb β, Bands of higher molecular weight than expected are detected corresponding probably to oligomers. M: SeeBlue Prestrained marker (Invitrogen), 1: Hep-25His (having the sequence of SEQ ID NO. 6), 2: Hep-25MycHis (having the sequence of SEQ ID NO. 8), 3: Hep-20MycHis (having the sequence of SEQ ID NO. 7).

Figure 3:
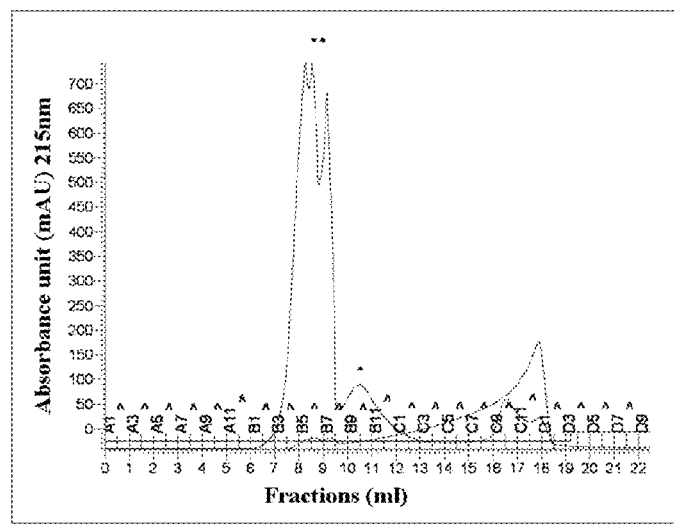

FIG. 3. Size exclusion chromatography of Hep25-His on a Superdex peptide column.

Size exclusion chromatography of Ni-NTA purified Hep-25His (having the sequence of SEQ ID NO. 6) was performed with a Peptide Superdex column on a FPLC AKTA system (Amersham Biosciences). The first peak (**) corresponds to oligomers of the Ni-NTA purified peptide and the second peak (*) to the monomer fraction, at 215 nm absorbance.

Figure 4:
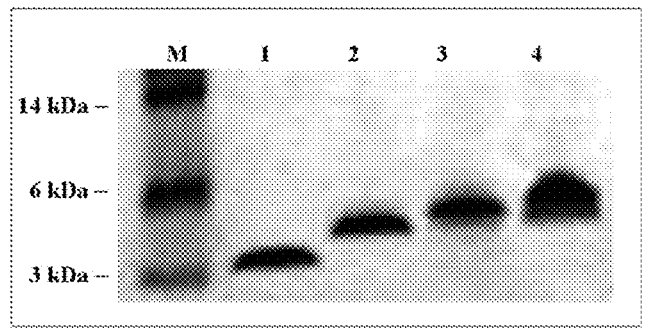

FIG. 4. Analysis of purified tagged hepcidin monomers after size exclusion chromatography. Purified tagged hepcidins were analysed on a Nu-PAGE 4-12% gel under non-denaturing conditions, followed by Coomasie blue staining. M: SeeBlue Prestrained marker (Invitrogen), 1: synthetic Hepcidin (Peptides International), 2: Hep-25His having the sequence of SEQ ID NO. 6 (4 kDa), 3: Hep-25MycHis having the sequence of SEQ ID NO. 8 (4.8 kDa), 4: Hep-20MycHis having the sequence of SEQ ID NO. 7 (5.2 kDa). The finally purified recombinant hepcidins migrate as monomers with the expected molecular mass.

Figure 5:
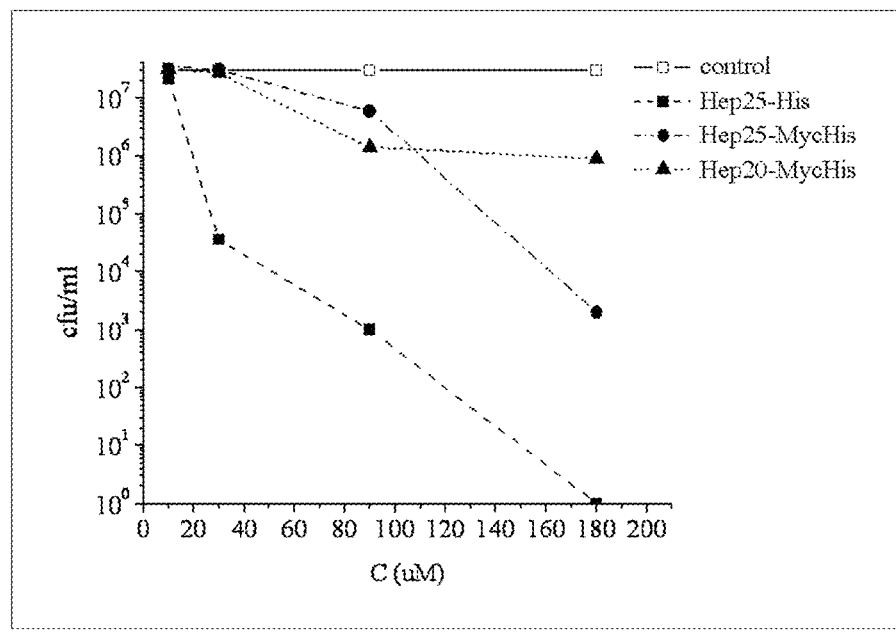

FIG. 5. Antimicrobial activity of recombinant tagged hepcidins. *E. coli* strain ML35 was subjected to CFU assay in order to determine the antimicrobial activity of synthetic hepcidin 25 (s. Hep25) having the sequence os SEQ ID NO. 2, Hep-25His having the sequence of SEQ ID NO. 6, Hep-25MycHis having the sequence of SEQ ID NO. 8, Hep-20MycHis having the sequence of SEQ ID NO. 7 and negative peptide having the sequence SEQ ID NO. 9 at the concentrations indicated for 2 h at 37° C. Sodium phosphate buffer was used as negative control.

Figure 6:
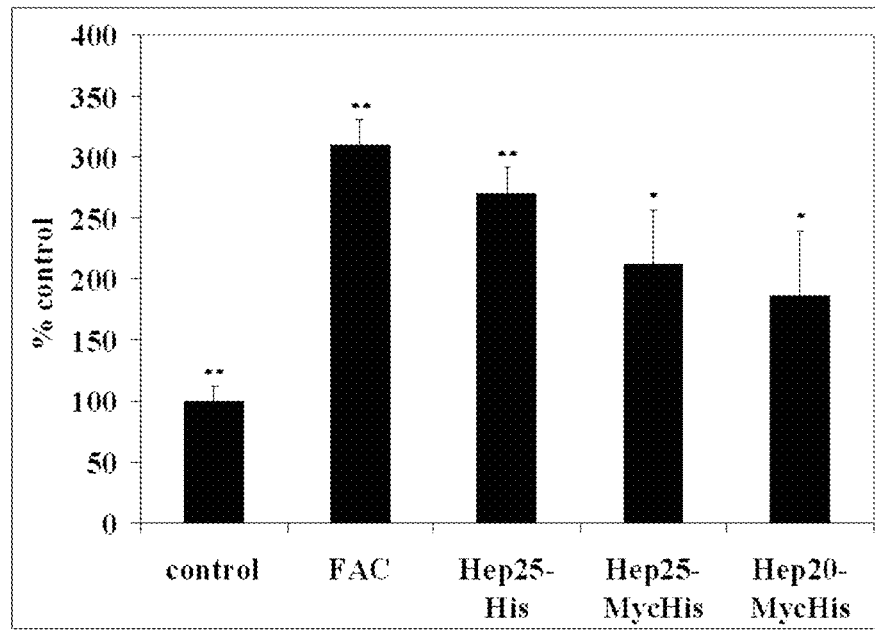

FIG. 6. Recombinant tagged hepcidins increase the Labile Iron Pool in RAW 264.7 macrophages. RAW 264.7 macrophages were treated with 10 μM Hep-25His having the sequence of SEQ ID NO. 6, Hep-25MycHis having the sequence of SEQ ID NO. 8, Hep-20MycHis having the sequence of SEQ ID NO. 7 and negative peptide having the sequence of SEQ ID NO. 9 for 4 h at 37° C. PBS was used as negative and FAC at 30 μg/ml as positive control. Relative alterations of the LIP were monitored with calcein upon addition of isonicotinoyl-hydraxone salicylaldehyde. Data are expressed as mean±S.D. of two independent experiments performed in triplicates relative to control. **$p<0.001$, *$p<0.05$. Statistical analysis was performed with t-Test.

Figure 7:
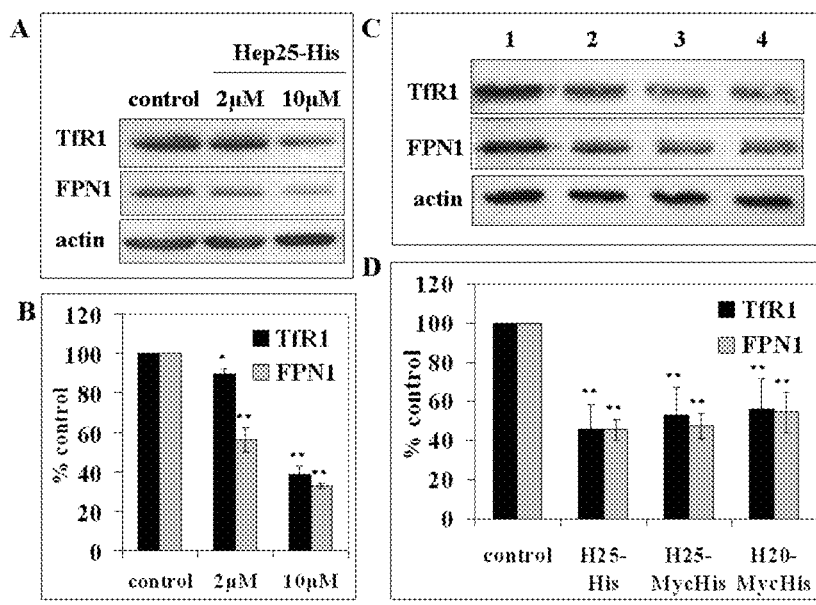

FIG. 7. Recombinant tagged hepcidins downregulate ferroportin and TfR1 in RAW 264.7 macrophages.

A, RAW 264.7 macrophages were treated with 11 μM and 10 μM of synthetic hepcidin-25 (having the sequence of SEQ ID NO. 2) and Hep-25His (having the sequence of SEQ ID NO. 6) for 4 h at 37° C. or with PBS as negative control. Cell lysates were subjected to 8% SDS PAGE and Western Blot with antibodies against TfR1, Ferroportin and actin as loading control. B, The signal density of ferroportin, TfR1 and actin protein bands from two independent experiments were quantified by densitometry and their intensity relative to actin was calculated. Data are expressed as mean of ratios of TfR1 or to actin levels ±S.D. for each experimental condition. *p<0.01. Statistical analysis was performed with the t-test, C,) Hep25-His binds specifically to FPNI. Hep25-His, negative peptide and PBS was incubated with Raw 264.7 macrophages, followed by cross-linking with DSS. Cell lysates were incubated with Ni2-NTA and eluates were analyzed by Western blot using anti-FPN1 Ab. D, Hep25-His causes the internalization of FPN1-GFP. HEK293-Fpn cells were induced with ponasterone for 24 h and then treated with Hep25-His or synthetic hepcidin 25 (s. Hep25) for 3 h. Fluorescence was visualized with a Leica TCS confocal microscope.

Figure 8:
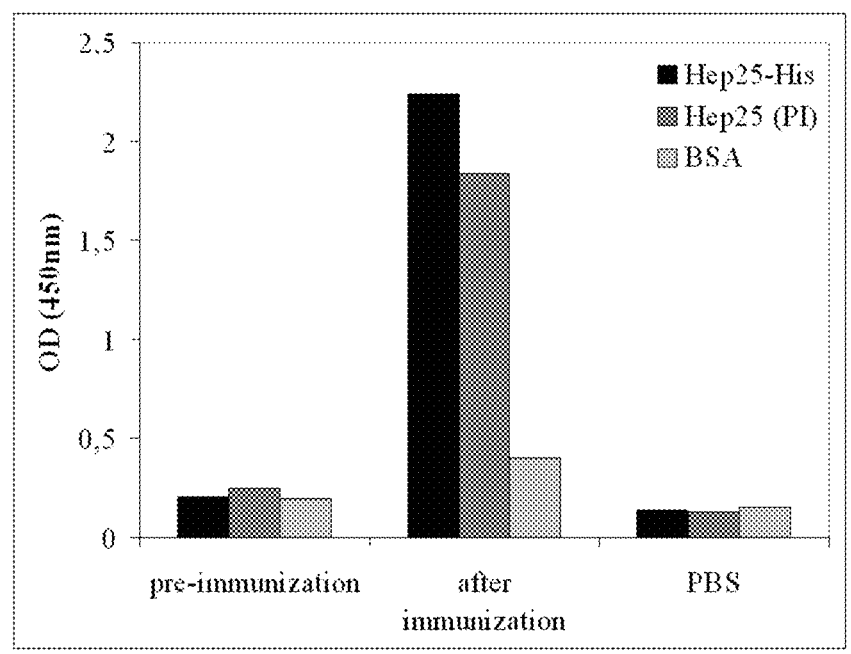

FIG. 8. Specificity of polyclonal serum against Hepcidin-25. Polyclonal serum was tested in ELISA, before and after each purification step, for binding to Hep-25His (having the sequence of SEQ ID NO. 6), synthetic peptide (Peptides International, PI) and BSA as negative controls.

Figure 9:
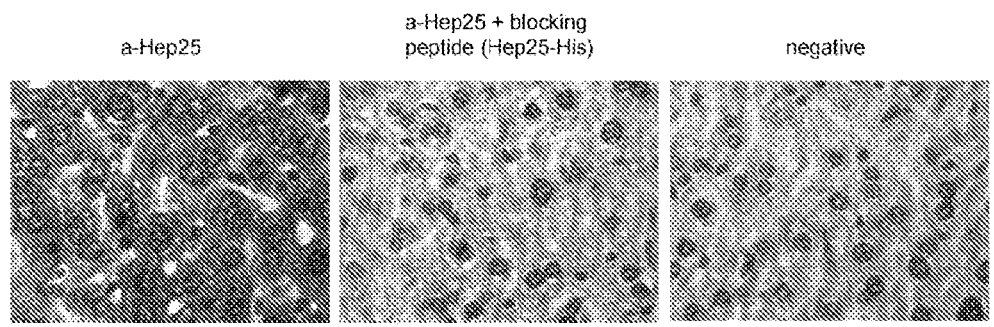

FIG. 9. Immunohistochemical staining of liver tissue sections using the polyclonal antibody against hepcidin25-His (a-Hep25). Secondary anti-rabbit antibody was used as negative control (negative). The specificity of the polyclonal antibody was verified after blockage of the signal following pre-incubation with hepcidin25-His.

Figure 10:
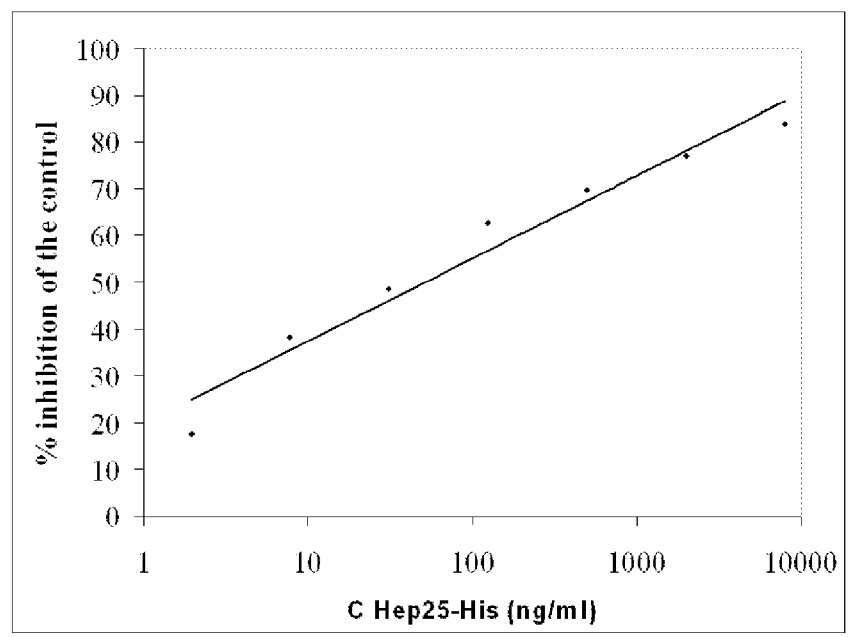

FIG. 10. Standard curve of inhibition ELISA, using increasing concentrations of soluble recombinant Hep25-His. Polyclonal antiserum against Hep25, diluted 1:3000 in PBS, 3% BSA, was pre-incubated with various amounts of Hep-25His (having the sequence of SEQ ID NO. 6) in solution (0.005-0.5 ng/ml), overnight at 4° C. Next day, complexes were added to Hep-25His-coated wells and left to compete for 1 h, at 37° C. A concentration dependent inhibition of antiserum binding was observed. All samples were tested in quadruplicates.

Figure 11:
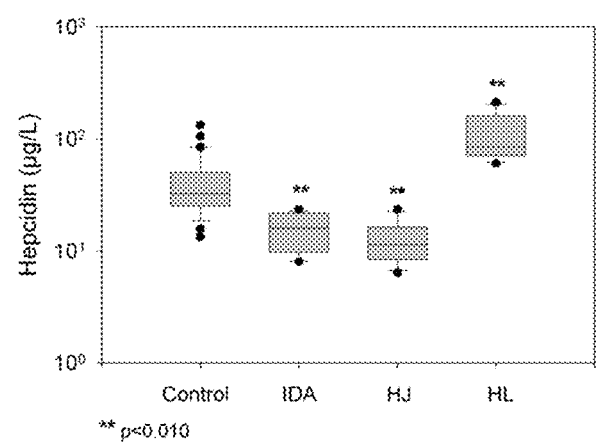

FIG. 11. Hepcidin serum concentration in healthy controls (control) and patients with juvenile haemochromatosis (JH). Box plots show the 25th and 75th percentile with median value for each group. Minimum and maximum values are also depicted. The difference compared to control is significant according to non-parametric Mann-Whitney test (SPSS 16.0 software).

FIG. 12. Recites the amino acid sequences of hepcidin-20 (SEQ ID NO.1), hepcidin-25 (SEQ ID NO.2); the hepcidin derivates hepcidin-20d (SEQ ID NO. 3), hepcidin-25d (SEQ ID NO. 4); and the tagged hepcidin derivatives hepcidin-20His (SEQ ID NO. 5), hepcidin-25His (SEQ ID NO. 6), hepcidin-20MvcHis (SEQ ID NO. 7), hepcidin-25MvcHis (SEQ ID NO. 8) and negative peptide (SEQ ID NO. 2):

```
                                        SEQ ID NO. 1
ICIFCCGCCHRSKCGMCCKT

SEQ ID NO. 2
DTHFPICIFCCGCCHRSKCGMCCKT

SEQ ID NO. 3
GAICIFCCGCCHRSKCGMCCKT

SEQ ID NO. 4
GADTHFPICIFCCGCCHRSKCGMCCKT

SEQ ID NO. 5
GAICIFCCGCCHRSKCGMCCKTFDHHHHHH
```

```
                                        SEQ ID NO. 6
GADTHFPICIFCCGCCHRSKCGMCCKTFDHHHHHH

SEQ ID NO. 7
GAICIFCCGCCHRSKCGMCCKLEQKLISEEDLNSAVDHHHHHH

SEQ ID NO. 8
GADTHFPICIFCCGCCHRSKCGMCCKLEQKLISEEDLNSAVDHHHHHH

SEQ ID NO. 9
SMNSRGPAGRLGSVPRAAAAASFLEQKLISEEDLNSAVDHHHHHH
```

EXPERIMENTAL PROCEDURES

Plasmid construction for expression of untagged and tackled hepcidins—Hepcidin-25 (75 bp) was synthetically constructed by extension of two overlapping oligonucleotides of 78 and 80 bases long and then by PCR amplification using specific primers.

FIG. 1 shows the sequence of the overlapping oligonucleotides ForHep25, that included an XhoI site along with the KEX2 cleavage site of the signal sequence, and RevHeplong, that included a NotI site and stop codon.

After extension of the overlapping oligonucleotides, PCR amplification was 15 performed using the For XhoI and RevNotI primers (FIG. 1). The resulting PCR product was subsequently inserted into XhoI-NotI sites of pPICZαC vector (Invitrogen, Carlsbad, Calif.) so that the recombinant peptide is led to soluble expression by a leader peptide a-factor under the transcriptional control of the AOX promoter.

The cloned Hep-25-pPICZαC vector was used as a template for the PCR amplification of hepcidin-20 (60 bp) using the specific upstream primer. Forhep20 (5-GCGAGTG-CATCGACGGCGCCATATGCATCTTCTGCTG-3) and the previously described RevHeplong primer.

Both constructs carried a stop codon just before the c-myc and 6xHis epitope 25 of the pPICZαC vector to allow expression of hepcidins without tags. The resulting recombinant plasmids, Hep-25 and Hep-20, were subjected to proper enzymatic modifications in order to produce the tagged constructs. The unique FokI restriction site of the insert in combination with the XbaI and SaII restriction sites from the vector were used for the construction of Hep-25MycHis, Hep-20MycHis, Hep-25His and 30 Hep-20His plasmids, which permitted the expression of hepcidin-20 (having the sequence of SEQ ID NO. 1), hepcidin-25 (having the sequence of SEQ ID NO. 2), hepcidin-20d (having the sequence of SEQ ID NO. 3) and hepcidin-25d (having the sequence of SEQ ID NO. 4) fused to c-MycHis or His epitope alone (including the WO 2009/027752 PCT/GR2008/000056 tagged hepcidin and tagged hepcidin derivatives having the sequences of SEQ.ID NOs. 5 to 8).

All DNA manipulations were performed as described (Sambrook J., Maniatis T., Fritsch E. F., Molecular Cloning: A Laboratory Manual, second ed. Cold Spring Harbor Laboratory Press, Cold Spring Harbor, N.Y., 1989.) and all constructs were verified by DNA sequencing.

All recombinant plasmids were linearized using PmeI restriction enzyme and transformed into strain X33 of *P. pastoris* (Invitrogen, Carlsbad, Calif.) by electroporation (Biorad, Hercules, Calif.). Selection was achieved on YPD (1% yeast extract, 2% peptone, 2% dextrose) agar plates containing 100 µg/ml Zeocin (Invitrogen, Carlsbad, Calif.) after 3 days of incubation at 30° C. Expression in *P. pastoris*—Several individual clones from each electroporation were incubated in 2 ml BMGY (1% yeast extract, 2% peptone, 0.1M potassium phosphate buffer pH 6.0, 1.34% YNB, $4 \times 10^{-5}$% biotin and 1% Glycerol) for 16 h at 30° C., and then the cells were resuspended in 2 ml BMMY (0.5% Methanol instead of glycerol) to induce expression.

After induction for 5 days with daily addition of methanol (0.5% v/v), the culture supernatants were tested for expression of hepcidin by dot blot analysis using a polyclonal anti-Hepcidin antibody (Alpha Diagnostics, San Antonio, Tex.) for the untagged peptides and a mAb anti-His (Amersham Biosciences, Piscataway, N.J.) or anti-Myc 9E.10 mAb (ATCC) for the tagged ones. The clones with the highest yield were used for large scale expression. In all subsequent preparations, cells were harvested at 36 h of methanol induction.

Purification and analysis of peptides—Culture supernatants were filtered through a 0.22 μm filter (Millipore, Bedford, Mass.), concentrated and dialyzed against 50 mM sodium phosphate buffer, 150 mM NaCL, with TFF Prep scale Ultrafiltration system equipped with 1 kDa filter (Millipore, Bedford, Mass.). The untagged hepcidins were subjected to size-exclusion chromatography performed on a Sephadex G-10 column (Amersham Biosciences, Piscataway, N.J.), as previously described (Tomosugi, N., Kawabata, H., Wakatabe, R., Higuchi, M., Yamaya, H., Umehera, H., Ishikawa, I. (2006) Blood 108, 1381-7). First-step purification of the 6xHIS containing peptides was performed with Ni-NTA metal affinity chromatography according to manufacturer's instructions (Qiagen, Valencia, Calif.). Elution was performed under native conditions with 50 mM sodium phosphate buffer pH 8.0, 150 mM NaCl, 250 mM Imidazole. The eluates were concentrated through lyophilization and subjected to size exclusion chromatography with a Peptide Superdex column (Amersham Biosciences, Piscataway, N.J.), specific for the separation of peptides 100-7000 Da, according to the manufacturer's instructions, for the isolation of hepcidin monomers. All size exclusion chromatography analysis was performed on an FPLC AKTA system (Amersham Biosciences, Piscataway, N.J.). Peptides were subjected to electrophoresis on 4-12% NuPAGE Novex Bis/Tris gels under non reducing conditions according to manufacture's instructions (Invitrogen, Carlsbad, Calif.) followed by Coomasie Brilliant Blue staining. Western blot of the tagged hepcidins was performed using an XCell II blot module according to manufacturer's instructions (Invitrogen, Carlsbad, Calif.). A Protran nitrocellulose membrane (Schleicher & Schuell, Dassel, Germany) with 0.1 μm pore size was used for transfer of the peptides followed by probing with anti-His MAb, in a dilution of 1:1000. Anti-mouse secondary antibody conjugated with HRP (in a dilution of 1:5000) was purchased by DakoCytomation (Carpinteria, Calif.). Quantification of purified hepcidins was performed with a fluorescent quantification system (Quant-It, Qubit), according to manufacturer's instructions (Invitrogen, Carlsbad, Calif.). Synthetic hepcidin25 used as control was purchased from Peptides International (Louisville, Ky.).

Antimicrobial assay—All purified recombinant hepcidins were tested for antibacterial activity against E. coli ML35 and BL21(DE) is a CFU assay (Porter E. M., van Dam E., Valore E. V., Ganz T., Broad-spectrum antimicrobial activity of human intestinal defensin 5, Infect. Immun. 65 (1997) 2396-2401.). Bacterial cell cultures were grown to $OD_{600}=0.2$ ($5 \times 10^7$ cfu/ml) and resuspended to a final concentration of $10^6$ cfu/ml in 20mM sodium phosphate buffer, pH7.4. Various concentrations of peptides were added to a final volume of 100 μl and after incubation for 2 h at 37° C., surviving cells were plated in triplicates to LB/agar plates.

Cell lines—THP-1 human and J774 murine monocytic cell lines were maintained in RPMI with 10% FBS, 2 mM L-glutamine, and 1% 30 penicillin/streptomycin solution at 37° C. and 5% $CO_2$ RAW 264.7 murine monocytic cell line and EcR293T transfected cells (kindly provided by Dr. Kaplan) (Nemeth, E., Tuttle, M. S., Powelson, J., Vaughn, M. B., Donovan, A., Ward, D. M. Ganz, T., Kaplan, J. (2004) Science 306, 2090-3), were maintained in DMEM (Gibco, USA) supplemented with 10% FBS, 2 mM L-glutamine, and 1% penicillin/streptomycin solution at 37° C. and 5% $CO_2$ 400 μg/ml zeocin (Invitrogen, Carlsbad, Calif.) and 400 μg/ml geneticin (Gibco, USA) were added to the stably transfected EcR293T cell line, in order to maintain selection of transfected Ferroportin-GFP under an ecdysone S promoter. Addition of 10 μM ponasterone (Sigma Chem, St Louis, Mass.) induced expression of ferroportin-GFP [10].

Western blotting—$1 \times 10^6$ cells (RAW 264.7, THP-1 or J774) were plated in E-well plates and after 12-20 h cells were treated with hepcidins in serum-free DMEM for 4 h, at 37° C. Afterwards, cells were re-suspended in lysis buffer (1% Triton, 25 mM Hepes pH 7.4, 150 mM NaCl, 10% Glycerol, 5 mM EDTA, 0.5 mM PMSF, protein inhibitors (Roche, Mannheim, Germany) and quantified by Bradford assay (Biorad, Hercules, Calif.). 30 μg of cell lysate was analyzed on 8% SDS-PAGE. Proteins were transferred to Hybond C nitrocellulose membrane (Amersham Biosciences, Piscataway, N.J.) and the membranes were incubated with the primary antibodies rabbit anti-ferroportin (Alpha Diagnostics, San Antonio, Tex.), mouse anti-TfR1 (Zymed, Invitrogen, Carlsbad, Calif.) and mouse anti-β actin (Santa Cruz Biotech, Santa Cruz, Calif.), in a dilution of 1:1000, overnight at 4° C. After washing, the membranes were incubated with anti-rabbit and anti-mouse secondary antibodies conjugated with HRP, in a dilution of 1:5000 (DakoCytomation, Carpinteria, Calif.), for 1 h at room temperature. Specific signal was detected with a chemiluminescence assay kit (ECL, Amersham Biosciences, Piscataway, N.J.). The bands were quantified by densitometry using the Quantity-One (Biorad, Hercules, Calif.) software. Data are shown as means±SD. Statistical analysis was performed by student t-Test.

LIP assay—The fluorescent metalosensor calcein (Molecular Probes, Eugene, Oreg.) was used for the measurement of alterations in the levels of the LIP (Labile Iron Pool) (Murphy, A. T., Witcher, D. R., Luan, P., and Wroblewski, V. J. (2007) Blood 110, 1048-54). $1 \times 10^6$ RAW 264.7 macrophages were plated in 6-well plates. After 16 h of incubation, recombinant hepcidin was added at 10 μM in serum-free DMEM for 4 h at 37° C., and then 0.25 μM calcein was added for 30 min at 25° C. Unbound calcein was washed away and cells were resuspended in cold PBS. Fluorescence was measured with the Perkin Elmer LS55 fluorescent plate reader (Perkin Elmer LifeSciences, Boston Mass.) (488 nm excitation, 517 nm emission). Quenching of extracellular calcein was achieved by the addition of 100 μM DFO. Intracellular calcein-bound iron was released upon addition of the fast-permeating iron chelator SIH (isonicotinyl hydrazone salicylaldehyde) at 100 μM. Relative changes were expressed as percentage of the control.

Cross-linking and pull-down assay Raw 264.7 cells were resuspended in ice-cold PBS at $2 \times 10^7$ cells/ml and Hep25-His, negative peptide or PBS were added at a final concentration of 10 mM for 1 h at 4_C. Disuccinimidyl suberate (DSS, Pierce, Rockford, Ill.) was added for 20 min at room temperature, followed by quenching with 20 mM TriseHCl pH 7.4 for 20 min. Protein lysate was extracted as described above and incubated with Ni2-NTA agarose overnight at 4_C. Bound proteins were eluted with 1 M imidazole and analyzed by Western blot using anti-FPN1 antibody as described above.

Immunization—A rabbit was immunized subcutaneously with 100 μg of Hep-25His dissolved in 0.4 ml of PBS and emulsified with an equal volume of Freund's complete adjuvant (Sigma Chem, St Louis, Mo.). The immunization protocol included 3 boost immunizations of one injection each where 100 μg of Hep-25His having the sequence of SEQ ID NO. 6 was dissolved in 0.4 ml of PBS and emulsified with an equal volume of Freund's incomplete adjuvant (Sigma Chem, St Louis, Mass.). A sample of pre-immune serum was taken from the ear vein before the first injection. The test bleeding was carried out 10 days after the last boost immunization from the ear vain. The serum was tested for antibody activity with ELISA assay.

Antibody purification—1 mg of 6xHis synthetic peptide (Covance, Princeton, N.J.) or 0.5 mg of Hep-25His peptide having the sequence of SEQ ID NO. 6 were coupled to CNBr-activated sepharose at 0.1 M $NaHCO_3$, pH 8.4, 0.5M NaCl, according to manufacturer's instructions (Pharmacia Biotech, Piscataway, N.J.).

Polyclonal antiserum against Hep-25His peptide having the sequence of SEQ ID NO. 6 was subjected to 33% saturated ammonium sulfate precipitation (Herbert, G. A., P. L. Pelham, and Pittman, B. (1973) *Appl. Microbiol.* 25, 26-36) and dialyzed against 50 mM sodium phosphate buffer, 150 mM Nacl. Afterwards, the serum was incubated overnight at 4° C. with 6xHis-coupled sepharose beads and then, the supernatant was retained, while the column was regenerated by washing twice with 0.2 N HCl-glycine, pH 2.8 and neutralized with 1 M $K_2HPO_4$. Finally the column was washed with 50 mM sodium phosphate buffer, 150 mM NaCl and stored at 4° C. in PBS, 0.02% azide. The above purification procedure was repeated 5 times. The resulting purified serum was further purified by incubation with Hep-25His-coupled sepharose column, overnight at 4° C. The next day, after washing the column twice with PBS, the specific anti-Hep25 antibodies were eluted with an equal volume of 0.2N HCl-glycine pH 2.7 and neutralized with 1 M Tris pH 9, 5 M NaCl.

Immunohistochemistry—In order to determine if the antibodies against hepcidin25-His could also identify native hepcidin we performed immunohistochemical analysis on normal mice liver tissues. Tissues were deparaffinized two times in xylene for 5 min and dehydrated in dilutions of ethanol (100%, 95%, 70%) for 2 min each. Endogenous peroxidase activity was quenched with 3% hydrogen peroxide for 30 min, followed by immersion in tap water for 5 min. Antigen retrieval was accomplished by immersing and heating the slides in 10 mM citrate buffer, pH 6.0 three times in a microwave, for 5 min each, after which they were allowed to cool to room temperature for 20 min. The slides were then incubated in blocking solution (3% FBS, 1% BSA, 0.05% Tween in TBS) for 30 min, followed by incubation with purified primary antibody (10 mg/ml) at 4° C. for 16 h. After that they were then incubated with secondary anti-rabbit antibody conjugated with HRP (diluted 1:100 in blocking buffer) (DakoCytomation, Carpinteria, Calif.) for 1 h. Visualization of the stain was accomplished after addition of 3,3' diaminobenzidine substrate (Sigma, St Louis, Mo.) for 5 min. The reaction was stopped by washing with tap water and slides were counterstained with Hematoxylin (Sigma, St Louis, Mo.) for 1 min. They were then dehydrated in a 70%, 95% and 100% ethanol series for 2 min each, cleared by immersing in xylene twice for 5 min each, and mounted in DPX (Sigma, St Louis, Mo.). Secondary antibody alone was used as negative control. In addition, competition experiments were performed by pre-incubating overnight at 4° C. the polyclonal antibody with Hep25-His peptide (1 mg/ml).

Enzyme-linked immunosorbent assay (ELISA)—Microtiter plates (96-well) (Costar, Corning, N.Y.) were coated overnight at 4° C. with 50 μl of Hep-25His (having the sequence of SEQ ID NO. 6), 6xHis or BSA (0.5 mg/ml) in 0.1 M sodium bicarbonate buffer (pH 8.6). Plates were washed and non-specific binding sites were blocked with blocking buffer (PBS containing 3% BSA) for 1 h at 37° C. Antiserum (diluted 1:3000 in PBS, 3% BSA) was added to each well, and the wells were incubated for 1 h at 37° C. For competition experiments, purified antiserum (diluted 1:3000 in PBS, 3% BSA) was overnight incubated with 8 μl of each human serum per well or various known concentrations of Hep-25His peptide (having the sequence of SEQ ID NO. 6) at 4° C. and next day, the complexes were added to wells and incubated for 1 h at 37° C., as well. Unbound antibody was removed by washing 10 times with PBST and plates were incubated with goat anti-rabbit IgG peroxidase conjugate (diluted 1:2000 in PBS, 3% BSA) (DakoCytomation, Carpinteria, Calif.) for 1 h at room temperature. The plates were washed as before and visualization of the signal was accomplished after addition of 3,3',5,5' tetramethylbenzidin (Pierce, Rockford, Ill.) for 10 min at room temperature. The reaction was stopped after the addition of 0.2 N sulphuric acid and color development was measured photometrically at 450 nm with a microplate reader (Bio-rad Model 680). All experiments were performed in quadruplicates.

Results

Soluble expression and purification of recombinant heocidins in yeast *P. pastoris*—Three different constructions were performed sequentially for recombinant soluble expression of hepcidin-20 and 25, in methylotrophic yeast *P. pastoris*: a) without tag peptide (Hep-20 and Hep-25 having the sequences of SEQ ID NOs. 1 and 2 respectively), b) with myc-His tags (Hep-20MycHis and Hep-25MycHis (having the sequences of SEQ ID NOs. 7 and 8 respectively) and c) with His tag (Hep-20His and Hep-25His having the sequences of SEQ ID NOs. 5 and 6 respectively), at the 3' end of the hepcidin sequences (FIG. 1). For each construct, several clones were induced by methanol for three days and culture supernatants were analyzed for hepcidin expression by dot blot immunoassay. The highest expressing clones were selected for large scale production. The recombinant peptides were harvested from culture supematants, concentrated and dialyzed by an ultrafiltration system (filter cut off 1 KDa), and the untagged and tagged peptides were purified by size-exclusion or $Ni^{2+}$-NTA metal affinity chromatography, respectively. In brief, no positive clones expressing the Hep-20His peptide were detected, whereas the yield of purified untagged hepcidin-20 and -25 was less than 20 μg/l. The low yield of the purified untagged peptides, that was approximately 20 ng per liter of culture, appears to be due to difficulties of purification and detection and not to their potentially toxicity of the expressing peptide. In contrast, the yield of Hep-25MycHis, Hep-20MycHis and Hep-25His tag peptides was approximately 5-7 mg/l of culture. Purified tagged products were analyzed on 4-12% NuPAGE gel and Coomassie Brilliant Blue staining (FIG. 2A). The molecular weight of Hep-25His is estimated at 4 kDa, of Hep-25MycHis at 5.2 kDa and of Hep-20MycHis at 4.8 kDa. The eluted peptides contained several higher molecular weight bands, which corresponded to oligomeric forms as confirmed by Western blot using the anti-myc or anti-His mAbs (FIG. 2B). In order to further purify the tagged hepcidins, FPLC size-exclusion chromatography was performed using a Superdex peptide column (Amersham Biosciences, Piscataway, N.J.) (FIG. 3). The resulting fractions corresponding to the molecular weight of interest were analyzed on a 4-12% Nu-PAGE gel (FIG. 4). The peptides migrated as monomers with a molecular mass consistent with that predicted from their amino acid sequence. The yield of the purified recombinant tagged hepcidin monomers was 0.5-1 mg/l of culture.

Antimicrobial activity of recombinant hepcidins—The colony forming unit assay (E. M. Porter, E. van Dam, E. V. Valore, T. Ganz, Broad-spectrum antimicrobial activity of human intestinal defensin 5, Infect. Immun. 65 (1997) 2396-2401) was used to determine the antimicrobial activity of the purified recombinant hepcidin forms against the *E. coli* strain, ML35. The *E. coli* BL21 (DE) strain, which is resistant to hepcidin, was used as the negative control. Surviving microbes were counted following incubation with various concentrations of recombinant hepcidin preparations, synthetic hepcidin or negative peptide for 2 h at 37° C. Recombinant untagged Hepcidin-20 (having the sequence of SEQ ID NO. 1) was bactericidal at concentrations higher than 10 mM, while Hepcidin-25 (having the sequence of SEQ ID NO. 2) could not be tested because it was produced in insufficient amounts (data not shown). From the tagged forms (FIG. 5), recombinant Hep25-His (having the sequence of SEQ ID NO. 6) presented the highest antibacterial activity (IC 50=15 mM), whereas the Myc epitope containing peptide Hep25-MycHis (having the sequence of SEQ ID NO. 8) was less effective (IC 50=58.6 mM), presumably due to significant alterations of its conformation. The antibacterial activity of Hep25-His (having the sequence of SEQ ID NO. 6) was comparable with that of the synthetic hepcidin 25 (having the sequence of SEQ ID NO. 2) (IC 50=9 mM) as shown in FIG. 5. None of them had any effect on the hepcidin resistant *E. coli* BL21(DE) strain. Originally filed FIGS. 6 and 7 have been swapped in position, thus, original FIG. 6 is now FIG. 7 and original FIG. 7 is now FIG. 6. This re-ordering of the original FIGS. 6 and 7 correspond to the original text and original figure legends. Original FIG. 8 is not being amending. Applicants have amended the FIG. 8 legend accordingly, which is show below and attached hereto:

Iron is accumulated in the RAWm 264.7 macrophages after treatment with recombinant hepcidin—The changes of cellular iron homeostasis after treatment with the recombinant hepcidins were also studied by Labile Iron Pool (LIP) assays (Konijn A. M., Glickstein H., Vaisman B., Meyron-Holtz E. G., Slotki I. N., Cabantchik Z. I, (1999) Blood 94, 2128-34). RAWm 264.7 macrophages were treated with the different forms of recombinant tagged hepcidin at 10 μM, for 4 h at 37° C. FAC (30 m/ml) was used as positive control and LIP was increased 3-fold (±0.2) (p<0.001) in comparison to untreated cells (FIG. 6). In the presence of Hep-25His (peptide having the sequence of SEQ ID NO. 6), LIP was increased approximately 2.5 fold (±0.21) (p<0.001), whereas Hep-25MycHis (peptide having the sequence of SEQ ID NO. 8) induced an increase of LIP of approximately 2-fold (±0.44) (p<0.05) (FIG. 6). Hep-20MycHis (peptide having the sequence of SEQ ID NO. 7) showed a lower effect on LIP, 1.85 fold (±0.52) (p<0.05). Hep25-His showed the most significant and consistent change in the LIP assay, while the Myc-containing peptides and great variance between experiments.

Recombinant hepcidins downregulate ferroportin and TfR1 in macrophages—The effect of recombinant hepcidins on cellular iron metabolism was tested in macrophage cells lines by measuring the expression levels of ferroportin (FPN1) and TfR1. RAW 264.7 cells were treated with 1 μM and 10 μM of hepcidin25 (having the sequence of SEQ ID NO. 2) and Hep-25His (having the sequence of SEQ ID NO. 6), the most active peptide in antibacterial assays and in LIP assays, for 4 h at 37° C. and the expression of FPN1 and TfR1 was detected in cell lysates by Western Blot analysis (FIG. 7). In comparison to untreated cells, Hep-25His at a concentration of 1 μM was able to reduce FPN1 by 37%±7, whereas at a concentration of 10 μM it reduced both TfR1 and FPN1 by 48%±17.7 and 48±3, respectively (FIG. 7A, B). The synthetic peptide caused an inhibition of TfR1 by 37%±6 and of FPN1 by 36%±10.6 at 10 μM. Higher concentrations of the recombinant peptide did not have a stronger effect (data not shown). The oligomeric fraction of Hep25-His was also tested and no effect was found on cellular iron metabolism (data not shown). Similar results were obtained when human THP-1 and murine J774 monocytic cells were treated with the recombinant peptides (data not shown). These results suggest that recombinant hepcidin can bind to FPN1 and induce its internalization and degradation (Nemeth, E., Tuttle, M. S., Powelson, J., Vaughn, M. B., Donovan, A., Ward, D. M. Ganz, T., Kaplan, J. (2004) *Science* 306, 2090-3), whereas TfR1 expression is reduced in order to minimize iron uptake.

Hep25-His acts by binding to ferroportin and causing its subsequent internalisation. The specific binding oh Hep25-His (having the sequence of SEQ ID NO. 6) to FPN1 was studied by a cross-linking and pull-down assay. RAW 264.7 were treated with He25-His (having the sequence of SEQ ID NO. 6) or negative peptide (having the sequence of SEQ ID NO. 9) at 10 nM, followed with cross-linking with DSS and pull-down using $Ni^2$-NTA agarose. Protein complex eluted from $Ni^2$-NTA was subjected to Western blot analysis using anti-ferroportin antibody. As shown in FIG. 7C, FPN1 was co-purified with Hep25-His after cross-linking and pull-down assay, thus suggesting that the recombinant Hep25-His peptide binds specifically to FPN1.

Furthermore, the internalization of FPN1 in the presence of Hep25-His (having the sequence of SEQ ID NO. 6) was analyzed in HEK293-Fpn cells by confocal microscopy; these cells express an FPN1-GFP fusion construct on the plasma membrane (Nemeth, E., Tuttle, M. S., Powelson, J., Vaughn, M. B., Donovan, A., Ward, D. M. Ganz, T., Kaplan, J. (2004) *Science* 306, 2090-3). Addition of recombinant Hep25-His (having the sequence of SEQ ID NO. 6) promoted the internalization of FPN1-GFP (FIG. 7D). Similar results were obtained when the synthetic Hep-25 peptide was used as positive control.

Production and purification of polyclonal antibody against Hepcidin—Polyclonal serum was raised against Hep-25His (peptide having the sequence of SEQ ID NO. 6) in rabbits. After 3 boosts, serum was tested for antibody activity with ELISA (FIG. 8). The polyclonal antiserum was subjected to 33% ammonium sulfate precipitation to specifically precipitate IgG immunoglobulin. The precipitated and dialyzed antiserum contained antibodies both against hepcidin and His peptide. In order to remove all anti-His antibodies, the antiserum was subjected to repeated passages from a 6His-coupled sepharose column. Supernatants from each purification step were tested in ELISA assay against H25His, 6xHis peptide and BSA (data not shown). The five times purified antiserum recognized specifically H25His peptide (FIG. 8). So did the antiserum that was further purified with Hep-25His-sepharoseIn order to determine its binding activity against native hepcidin we performed immunohistochemistry on paraffin embedded mouse liver sections (FIG. 9). The antibody showed a strong cytoplasmic staining that was abolished after preincubation with hepcidin25-His.

Competition ELISA assay—The recombinant peptide along with the antibody raised against it was used for the development of an immunological assay for the quantification of hepcidin in human serum. After determining the optimal concentration of antigen and antibody according to (J. R. Crowther, The ELISA guidebook, Methods Mol Biol 149 (2000) 1-413), we proceeded to the characterisation of our ELISA system.

Our inhibition ELISA produces a typical calibration curve for the recombinant hepcidin25-His, which is shown in FIG. 10. The analytical limit of detection of the ELISA assay, defined as the concentration corresponding to the mean signal+3 SD of 10 replicates of the zero calibrator was 5.4 µg/L. The measurement range was 10-1500 µg/L. For the statistical analysis of the reproducibility, linearity and recovery of the hepcidin ELISA assay, we used 3 serum samples ranging from low (22 µg/L) to high (150 µg/L) concentrations chosen from a large number of samples tested. The intra-assay CVs were 8-15% as evaluated by assaying 10 replicates of each sample in a single assay. The inter-assay CVs were 5-16% as evaluated by 7 subsequent measurements of the test samples. Analytical recovery was studied by adding the calibrator at 7.5, 30 and 75 µg/L in each serum sample and was found to range from 90-120% with a mean recovery index of 105%. Mean linearity was estimated at 97% after measuring 3 serial dilutions (1:2, 1:4, 1:8) of the 3 serum samples.

In order to determine whether our assay was providing biologically meaningful measurements, we tested serum samples from patients with anticipated low hepcidin levels (HJV associated juvenile haemochromatosis), compared to healthy controls.

Mean hepcidin concentration was significantly lower in 7 patients with juvenile haemochromatosis (12.8 µg/L, p<0.05) compared to age-matched healthy controls (34.3 µg/L), as shown in FIG. 11. Our results are in agreement with previous findings regarding the levels of hepcidin in this disorder and allow us to assume that this new ELISA system can effectively quantify hepcidin in serum. However, it is important to note that the fold change between or inside the groups was much lower in our assay compared to previous reports using other quantification techniques. This might be a limitation in distinguishing differences among samples with tight variations. Furthermore, the possibility of interaction of the polyclonal antibody with other forms of hepcidin, such as the truncated 20-aminoacid hepcidin, cannot be excluded.

The invention claimed is:

1. A method for producing biologically functional hepcidin or biologically functional hepcidin derivative, the method comprising the step of expressing hepcidin or hepcidin derivative within an expression system, wherein the expressing hepcidin or hepcidin derivative is an expressed hepcidin having a sequence of SEQ ID NO. 6.

2. The method of claim 1, wherein the method comprises a step of exogenously expressing a tagged biologically functional hepcidin or tagged biologically functional hepcidin derivative within an expression system, wherein the expression system is a eukaryotic methylotropic yeast.

3. The method of claim 2, wherein the eukaryotic methylotropic yeast is Pichia pastoris (P. pastoris).

4. The method of claim 2, wherein prior to expression, the method comprises a step of introducing a vector comprising a hepcidin encoding polynucleotide insert into the expression system, wherein the expression system is a eukaryotic methylotropic yeast expression system.

5. The method of claim 4, wherein the eukaryotic methylotropic yeast is Pichia pastoris (P. pastoris).

6. The method of claim 4, wherein the vector is pPICZαA, pPICZαB or pPICZαC.

7. The method of claim 1, wherein the method further comprises a two stage process, comprising a first stage and a second stage, for purifying an expressed hepcidin.

8. The method of claim 7, wherein the first stage comprises metal affinity chromatography.

9. The method of claim 8, wherein the metal is nickel or cobalt.

10. The method of claim 9, comprising immobilizing the nickel to the first stage by nitilotriacetic acid (NTA).

11. The method according to claim 7, wherein the second stage comprises gel filtration chromatography.

12. The method of claim 1, wherein the chromatography is a sepharose peptide column.

* * * * *

UNITED STATES PATENT AND TRADEMARK OFFICE
CERTIFICATE OF CORRECTION

| | | |
|---|---|---|
| PATENT NO. | : 8,614,068 B2 | Page 1 of 1 |
| APPLICATION NO. | : 12/675007 | |
| DATED | : December 24, 2013 | |
| INVENTOR(S) | : Avgi Mamalaki et al. | |

It is certified that error appears in the above-identified patent and that said Letters Patent is hereby corrected as shown below:

In the Claims

Column 24, Line 53, Claim 12:

After "The method of claim" delete "1" and
Insert -- 11 --.

Signed and Sealed this
Twenty-ninth Day of April, 2014

Michelle K. Lee
*Deputy Director of the United States Patent and Trademark Office*

```
                          SEQUENCE LISTING

<160> NUMBER OF SEQ ID NOS: 12

<210> SEQ ID NO 1
<211> LENGTH: 20
<212> TYPE: PRT
<213> ORGANISM: Homo sapiens

<400> SEQUENCE: 1

Ile Cys Ile Phe Cys Cys Gly Cys Cys His Arg Ser Lys Cys Gly Met
1               5                   10                  15

Cys Cys Lys Thr
            20

<210> SEQ ID NO 2
<211> LENGTH: 25
<212> TYPE: PRT
<213> ORGANISM: Homo sapiens

<400> SEQUENCE: 2

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 3
<211> LENGTH: 22
<212> TYPE: PRT
<213> ORGANISM: Homo sapiens

<400> SEQUENCE: 3

Gly Ala Ile Cys Ile Phe Cys Cys Gly Cys Cys His Arg Ser Lys Cys
1               5                   10                  15

Gly Met Cys Cys Lys Thr
            20

<210> SEQ ID NO 4
<211> LENGTH: 27
<212> TYPE: PRT
<213> ORGANISM: Homo sapiens

<400> SEQUENCE: 4

Gly Ala Asp Thr His Phe Pro Ile Cys Ile Phe Cys Cys Gly Cys Cys
1               5                   10                  15
```

His Arg Ser Lys Cys Gly Met Cys Cys Lys Thr
        20                  25

<210> SEQ ID NO 5
<211> LENGTH: 30
<212> TYPE: PRT
<213> ORGANISM: Homo sapiens

<400> SEQUENCE: 5

Gly Ala Ile Cys Ile Phe Cys Cys Gly Cys Cys His Arg Ser Lys Cys
1               5                   10                  15

Gly Met Cys Cys Lys Thr Phe Asp His His His His His
        20                  25                  30

<210> SEQ ID NO 6
<211> LENGTH: 35
<212> TYPE: PRT
<213> ORGANISM: Homo sapiens

<400> SEQUENCE: 6

Gly Ala Asp Thr His Phe Pro Ile Cys Ile Phe Cys Cys Gly Cys Cys
1               5                   10                  15

His Arg Ser Lys Cys Gly Met Cys Cys Lys Thr Phe Asp His His His
        20                  25                  30

His His His
    35

<210> SEQ ID NO 7
<211> LENGTH: 43
<212> TYPE: PRT
<213> ORGANISM: Homo sapiens

<400> SEQUENCE: 7

Gly Ala Ile Cys Ile Phe Cys Cys Gly Cys Cys His Arg Ser Lys Cys
1               5                   10                  15

Gly Met Cys Cys Lys Leu Glu Gln Lys Leu Ile Ser Glu Glu Asp Leu
        20                  25                  30

Asn Ser Ala Val Asp His His His His His His
        35                  40

<210> SEQ ID NO 8
<211> LENGTH: 48
<212> TYPE: PRT
<213> ORGANISM: Homo sapiens

<400> SEQUENCE: 8

Gly Ala Asp Thr His Phe Pro Ile Cys Ile Phe Cys Cys Gly Cys Cys
1               5                   10                  15

His Arg Ser Lys Cys Gly Met Cys Cys Lys Leu Glu Gln Lys Leu Ile
        20                  25                  30

Ser Glu Glu Asp Leu Asn Ser Ala Val Asp His His His His His His
        35                  40                  45

<210> SEQ ID NO 9
<211> LENGTH: 45
<212> TYPE: PRT
<213> ORGANISM: Homo sapiens

<400> SEQUENCE: 9

Ser Met Asn Ser Arg Gly Pro Ala Gly Arg Leu Gly Ser Val Pro Arg
1               5                   10                  15

-continued

```
Ala Ala Ala Ala Ala Ser Phe Leu Glu Gln Lys Leu Ile Ser Glu Glu
                20              25                  30

Asp Leu Asn Ser Ala Val Asp His His His His His
        35              40                  45

<210> SEQ ID NO 10
<211> LENGTH: 37
<212> TYPE: DNA
<213> ORGANISM: ARTIFICIAL
<220> FEATURE:
<223> OTHER INFORMATION: PCR Primer

<400> SEQUENCE: 10
gcgagtgcat cgacggcgcc atatgcatct tctgctg                        37

<210> SEQ ID NO 11
<211> LENGTH: 14
<212> TYPE: DNA
<213> ORGANISM: artificial
<220> FEATURE:
<223> OTHER INFORMATION: PCR Primer

<400> SEQUENCE: 11
ggaccgctcg agaa                                                 14

<210> SEQ ID NO 12
<211> LENGTH: 19
<212> TYPE: DNA
<213> ORGANISM: artificial
<220> FEATURE:
<223> OTHER INFORMATION: PCR Primer

<400> SEQUENCE: 12
gcgagtcatt ctgcggccg                                            19
```